(12) United States Patent
Kent et al.

(10) Patent No.: US 9,429,937 B2
(45) Date of Patent: *Aug. 30, 2016

(54) SYSTEMS AND METHODS FOR DETECTING AND REJECTING DEFECTIVE ABSORBENT ARTICLES FROM A CONVERTING LINE

(71) Applicant: The Procter & Gamble Company, Cincinnati, OH (US)

(72) Inventors: Jeffrey Michael Kent, Lebanon, OH (US); Louis J. Cedrone, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 233 days.

This patent is subject to a terminal disclaimer.

(21) Appl. No.: 14/215,115

(22) Filed: Mar. 17, 2014

(65) Prior Publication Data

US 2014/0200701 A1    Jul. 17, 2014

Related U.S. Application Data

(63) Continuation of application No. 13/402,205, filed on Feb. 22, 2012, now Pat. No. 8,712,570, which is a continuation of application No. 12/476,553, filed on Jun. 2, 2009, now Pat. No. 8,145,338.

(51) Int. Cl.
*G05B 19/418* (2006.01)
*A61F 13/15* (2006.01)

(52) U.S. Cl.
CPC ... *G05B 19/41875* (2013.01); *A61F 13/15772* (2013.01); *G05B 2219/31284* (2013.01); *Y02P 90/14* (2015.11)

(58) Field of Classification Search
CPC .............. G05B 19/41875; G05B 2219/31284; G05B 19/182; A61F 13/15772; Y02P 90/14
See application file for complete search history.

(56) References Cited

U.S. PATENT DOCUMENTS

| 5,286,543 A | 2/1994 | Ungpiyakul et al. |
| 5,359,525 A | 10/1994 | Weyenberg |

(Continued)

FOREIGN PATENT DOCUMENTS

| EP | 1528907 B1 | 9/2008 |
| WO | WO 2007/105938 A1 | 9/2007 |

(Continued)

OTHER PUBLICATIONS

Ken Harris, "An Application of IEEE 1588 to Industrial Automation," Rockwell Automation Publication 1756-WP005A-En-E, Jan. 2009.

(Continued)

*Primary Examiner* — Ramesh Patel
(74) *Attorney, Agent, or Firm* — Charles R. Matson

(57) ABSTRACT

The present disclosure relates to systems and processes for detecting and rejecting defective absorbent articles from a converting line. In particular, the systems and methods may utilize feedback from technologies, such as vision systems, sensors, remote input and output stations, and controllers with synchronized embedded clocks to accurately correlate inspection results and measurements from an absorbent article converting process. As such, the systems and methods may accurately apply the use of precision clock synchronization for both instrumentation and control system devices on a non-deterministic communications network. In turn, the clock synchronized control and instrumentation network may be used to control a reject system on converters of absorbent articles. In some embodiments, the controller will reject only defective absorbent articles without the need to reject non-defective absorbent articles.

18 Claims, 8 Drawing Sheets

(56) References Cited

U.S. PATENT DOCUMENTS

| | | | | |
|---|---|---|---|---|
| 5,980,087 | A * | 11/1999 | Brandon | A61F 13/15772 226/2 |
| 6,450,321 | B1 | 9/2002 | Blumenthal et al. | |
| 6,705,453 | B2 | 3/2004 | Blumenthal et al. | |
| 6,764,563 | B2 * | 7/2004 | Henry | B65H 23/1886 156/229 |
| 6,801,828 | B2 | 10/2004 | Popp et al. | |
| 6,811,019 | B2 | 11/2004 | Christian et al. | |
| 6,814,217 | B2 | 11/2004 | Blumenthal et al. | |
| 6,820,022 | B2 | 11/2004 | Popp et al. | |
| 6,829,516 | B2 | 12/2004 | Popp et al. | |
| 6,845,278 | B2 | 1/2005 | Popp et al. | |
| 6,888,083 | B2 * | 5/2005 | Hergeth | G01N 21/8903 156/64 |
| 6,909,106 | B2 * | 6/2005 | Ungpiyakul | A61F 13/15772 250/559.32 |
| 7,082,347 | B2 * | 7/2006 | Popp | A61F 13/15772 700/124 |
| 7,123,981 | B2 | 10/2006 | Dollevoet et al. | |
| 7,162,319 | B2 * | 1/2007 | Popp | A61F 13/15772 493/11 |
| 7,171,283 | B2 * | 1/2007 | Popp | G05B 19/042 162/273 |
| 7,187,995 | B2 * | 3/2007 | Floeder | G01N 21/89 382/141 |
| 7,797,133 | B2 * | 9/2010 | Floeder | G01N 21/89 382/141 |
| 7,882,438 | B2 * | 2/2011 | Markham | A23Q 35/12 700/106 |
| 7,982,764 | B2 * | 7/2011 | Kadaba | G05B 19/0428 348/125 |
| 8,145,338 | B2 * | 3/2012 | Kent | A61F 13/15772 226/10 |
| 8,145,343 | B2 * | 3/2012 | DeBruler | A61F 13/15772 226/10 |
| 8,145,344 | B2 * | 3/2012 | Debruler | G05B 19/182 226/10 |
| 8,712,573 | B2 * | 4/2014 | DeBruler | A61F 13/15772 226/10 |
| 8,712,574 | B2 * | 4/2014 | DeBruler | A61F 13/15772 226/10 |
| 2003/0169424 | A1 * | 9/2003 | Vogt | A61F 13/15756 356/429 |
| 2004/0019400 | A1 * | 1/2004 | Popp | A61F 13/15772 700/125 |
| 2004/0022426 | A1 * | 2/2004 | Carbone, II | G06T 7/0004 382/141 |
| 2004/0030432 | A1 * | 2/2004 | Popp | A61F 13/15772 700/109 |
| 2004/0083018 | A1 | 4/2004 | Dollevoet et al. | |
| 2004/0089516 | A1 * | 5/2004 | Christian | A61F 13/15723 198/459.8 |
| 2005/0043841 | A1 * | 2/2005 | Popp | A61F 13/15772 700/110 |
| 2005/0125180 | A1 * | 6/2005 | Miller | A61F 13/15723 702/94 |
| 2005/0154485 | A1 * | 7/2005 | Popp | A61F 13/15772 700/124 |
| 2005/0217791 | A1 * | 10/2005 | Costello | A61F 13/15585 156/277 |
| 2006/0047705 | A1 * | 3/2006 | Reade | B23Q 35/15 |
| 2008/0132865 | A1 * | 6/2008 | Li | A61F 13/15 604/378 |
| 2008/0223537 | A1 * | 9/2008 | Wiedmann | A61F 13/15747 162/198 |
| 2010/0305738 | A1 * | 12/2010 | DeBruler | A61F 13/15772 700/105 |
| 2012/0150331 | A1 * | 6/2012 | DeBruler | G05B 19/182 700/108 |
| 2012/0150332 | A1 | 6/2012 | DeBruler et al. | |
| 2012/0150336 | A1 | 6/2012 | Kent et al. | |

FOREIGN PATENT DOCUMENTS

| | | |
|---|---|---|
| WO | WO 2007/126345 A1 | 11/2007 |
| WO | WO 2007/126347 A1 | 11/2007 |
| WO | WO 2012/125526 A1 | 9/2012 |

OTHER PUBLICATIONS

"Precision clock synchronization protocol for networked measurement and control systems," IEEE 1588, First edition, 2004.

Dopplinger et al., "Aligning System Clocks Over Networks With IEEE 1588 Remote Timing Standard," Analog Zone, 2006.

Pastorius et al., "High-speed tire inspection," Tire Technology InternationaL, 2007, pp. 149-150.

http://zone.ni.com/devzone/cda/tut/p/id/2822; "Introduction to Distributed Clock Synchronization and the IEEE 1588 Precision Time Protocol," May 14, 2008, pp. 1-6.

http://www.automation.com/smc/print.php?stripImages=no; "Today's Automation News Headlines from Automation.com," Dec. 16, 2008.

Paul G. Schreier, http://www.entrepreneur.com/tradejournals/article/print/197678918.html, "IEEE 1588 to transform timing synchronization," Entrepreneur; Apr. 2009, pp. 1-6.

PCT International Search Report dated Sep. 17, 2010, 15 pages.

U.S. Appl. No. 12/476,348, filed Jun. 2, 2009—Notice of Allowance and Notice of Allowability mailed Aug. 10, 2011, (9 pages).

U.S. Appl. No. 12/476,348, filed Jun. 2, 2009—Supplemental Notice of Allowability mail Sep. 15, 2011 (5 pages).

U.S. Appl. No. 12/476,479, filed Jun. 2, 2009—Office Action mailed Aug. 15, 2011, (8 pages).

U.S. Appl. No. 13/402,233, filed Feb. 22, 2012—Office Action mailed Aug. 27, 2013, (10 pages).

U.S. Appl. No. 13/402,251, filed Feb. 22, 102—Office Action mailed Aug. 27, 2013 (5 pages).

* cited by examiner

SYSTEMS AND METHODS FOR DETECTING AND REJECTING DEFECTIVE ABSORBENT ARTICLES FROM A CONVERTING LINE

CROSS REFERENCE TO RELATED APPLICATIONS

This application is a continuation of U.S. application Ser. No. 13/402,205, filed on Feb. 22, 2012, which is a continuation of U.S. application Ser. No. 12/476,553, filed Jun. 2, 2009, now U.S. Pat. No. 8,145,338, which are all hereby incorporated by reference.

FIELD OF THE INVENTION

The present disclosure relates to systems and methods for manufacturing disposable absorbent articles, and more particularly, systems and methods for detecting and rejecting defective absorbent articles from a converting line.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

For quality control purposes, absorbent article converting lines may utilize various types of sensor technology to detect various types of defects in the webs and discrete components added to the webs along the converting line as absorbent articles are constructed. Example sensor technology may include vision systems, photoelectric sensors, proximity sensors, laser or sonic distance detectors, and the like. Sensor data may be communicated to a controller in various ways. In turn, the controller may be programmed to receive sensor data and reject or cull defective diapers after the final knife cut at the end of the converting line.

However, the controller may not be able to track the exact locations of defects in the web and corresponding diapers with a very large degree of accuracy due to slow sensor and control loop times. For example, the sensor and control technologies may work asynchronously of each other, thus creating control system accuracy challenges, which may be exacerbated at the high speed production rates of some absorbent article processes. For example, if data from a sensor is received by a controller after a processing cycle has begun, the data will not be evaluated in the controller until after the next input cycle has been reached. As such, a window in time is created during which an event may be sensed but not acted upon in the controller. To compensate, the controller may be programmed to assume that the event happened at anytime within the previous processing cycle. Thus, in order to account for the controller's poor ability to track a defect, it may be necessary to reject a relatively large number large number diapers to the front and the rear of a detected defect location in order to provide a high degree of confidence that the actual defective absorbent article is being rejected. As a result, a large number of non-defective articles may be rejected when attempting to reject defective articles. In addition, compensating for the aforementioned time delays may be further complicated when the communication and processing cycles are asynchronous and variable, which prevents deterministic calculation of the delay between sensor detection of an event and the availability of the data to be evaluated by the processor.

SUMMARY OF THE INVENTION

The present disclosure relates to systems and processes for detecting and rejecting defective absorbent articles from a converting line. In particular, the systems and methods may utilize feedback from technologies, such as vision systems, sensors, remote input and output stations, and controllers with synchronized embedded clocks to accurately correlate inspection results and measurements from an absorbent article converting process. As such, the systems and methods may accurately apply the use of precision clock synchronization for both instrumentation and control system devices on a non-deterministic communications network. In turn, the clock synchronized control and instrumentation network may be used to control a reject system on converters of absorbent articles. In some embodiments, the controller will reject only defective absorbent articles without the need to reject non-defective absorbent articles.

In one form, a method for rejecting defective absorbent products from a web converting manufacturing process includes the steps of: providing a communication network; connecting a sensor with the communication network, the sensor including a sensor clock; connecting a controller with the communication network, the controller including a controller clock; synchronizing the sensor clock with the controller clock such that the reported time of the controller clock and the sensor clock can be correlated; advancing a substrate in a machine direction through a converting process at a first speed; virtually segmenting the substrate into a plurality of virtual products along the machine direction; virtually dividing the virtual products into a plurality of virtual segments along the machine direction; sequentially adding component parts to the substrate; inspecting the substrate and component parts with the sensor; communicating inspection parameters from the sensor to the communication network; assigning a timestamp to each inspection parameter, each timestamp based on the sensor clock; receiving the inspection parameters and corresponding timestamps from the communication network into the controller; correlating each inspection parameter with one virtual segment based on the timestamp of the inspection parameter and the first speed of the substrate; identifying defects in virtual segments based on the inspection parameters; cutting the substrate with component parts added thereto into discrete absorbent articles; rejecting absorbent articles that correspond with virtual products having virtual segments with identified defects; and packaging absorbent articles that correspond with virtual products having virtual segments with no identified defects.

In another form, a method for rejecting defective absorbent products from a web converting manufacturing process includes the steps of: providing a communication network; connecting a sensor to a remote I/O station and connecting the remote I/O station to the network, the remote I/O station including a sensor clock; connecting a controller with the communication network, the controller including a controller clock; synchronizing the sensor clock with the controller clock such that the reported time of the controller clock and the sensor clock can be correlated; advancing a substrate in a machine direction through a converting process at a first speed; virtually segmenting the substrate into a plurality of virtual products along the machine direction; virtually dividing the virtual products into a plurality of virtual segments along the machine direction; sequentially adding component parts to the substrate; inspecting the substrate and component parts with the sensor; communicating inspection parameters from the sensor to the communication network; assigning a timestamp to each inspection parameter, each timestamp based on the sensor clock; receiving the inspection parameters and corresponding timestamps from the communication network into the controller; correlating each inspection parameter with one virtual segment based on the timestamp of the inspection parameter and the first speed of the substrate; identifying defects in virtual segments based on the inspection parameters; cutting the substrate with component parts added thereto into discrete absorbent articles; rejecting absorbent articles that correspond with virtual products having virtual segments with identified defects; and packaging absorbent articles that correspond with virtual products having virtual segments with no identified defects.

DETAILED DESCRIPTION OF THE INVENTION

Figure 1:
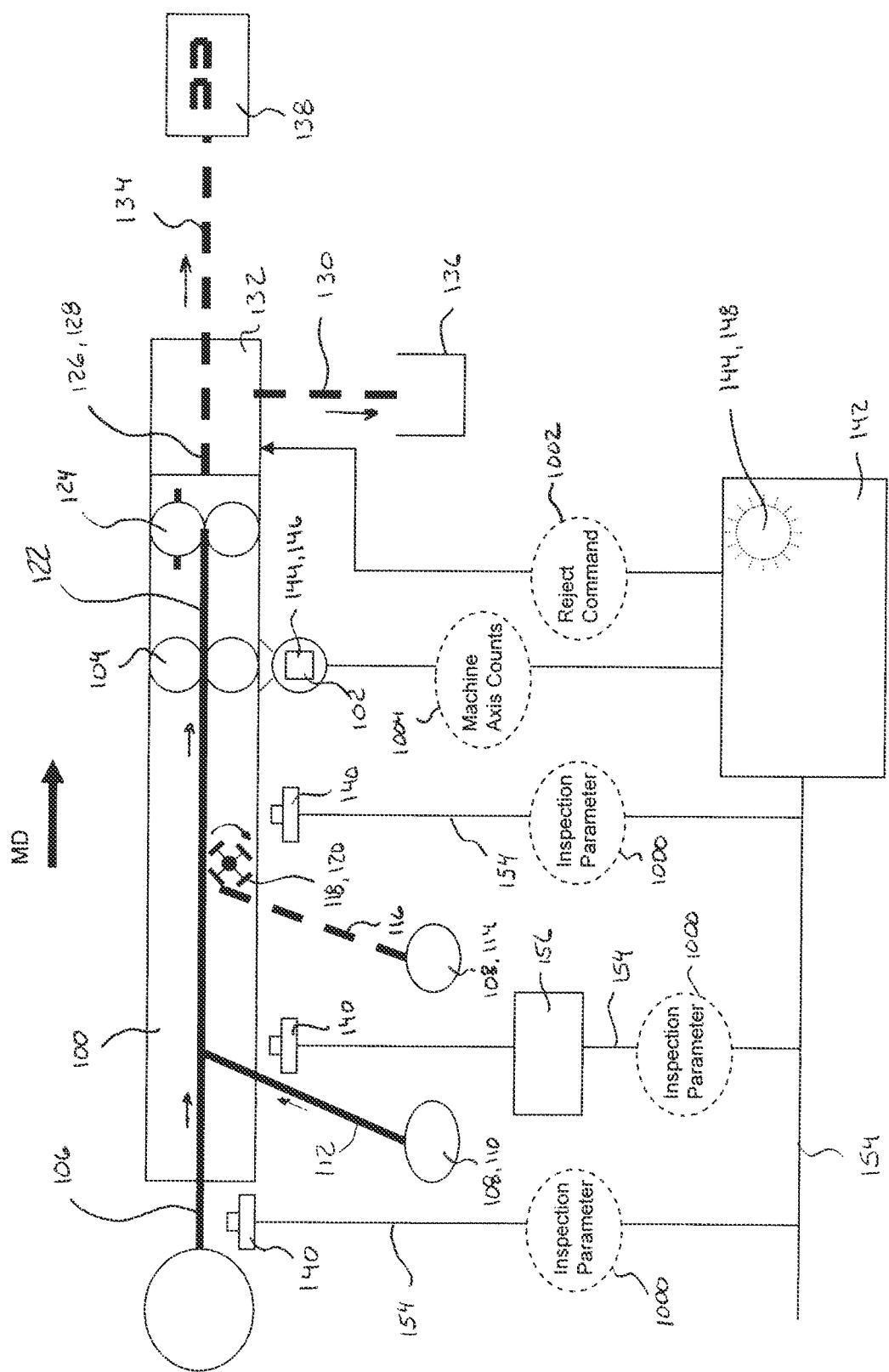
FIG. 1 is a schematic representation of an absorbent article converting line and reject system.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. The term "cross direction" (CD) is used herein to refer to a direction that is generally perpendicular to the machine direction.

The present disclosure relates to systems and processes for detecting and rejecting defective absorbent articles from a converting line. In particular, the systems and methods herein focus on creating a more accurate reject system with improved set-up, defect detection, defect tracking, and validation algorithms. For example, the systems and methods may utilize feedback from technologies, such as vision systems, sensors, remote input and output stations, and controllers with synchronized embedded clocks to accurately correlate inspection results and measurements from an absorbent article converting process. As such, the systems and methods may accurately apply the use of precision clock synchronization for both instrumentation and control system devices on a non-deterministic communications network, such as for example, an EthernetIP network. In turn, the clock synchronized control and instrumentation network may be used to control a reject system on converters of absorbent articles. Thus, the controller may be programmed to track defects in substrates and components along the converting line without having to account for undeterminable delays. In some embodiments, the controller will reject only defective absorbent articles without the need to reject non-defective absorbent articles.

Although the present disclosure is provided in the context of manufacturing absorbent articles, and diapers in particular, it is to be appreciated that the systems and methods disclosed herein may be applied to the manufacture of various types of articles and products involving the monitoring of various different types of substrates and/or components. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets such as the SWIFFER cleaning sheets, pre-moistened wipes or pads such as the SWIFFER WET pre-moistened cloths, paper towels such as the BOUNTY paper towels, dryer sheets such as the BOUNCE dryer sheets and dry-cleaning clothes such as the DRYEL cleaning clothes all sold by The Procter & Gamble Company. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers such as PAMPERS diapers, training and pull-on pants such as PAMPERS FEEL 'N LEARN and EASY UPS, adult incontinence briefs and undergarments such as ATTENDS adult incontinence garments, feminine hygiene garments such as panty liners, absorbent inserts, and the like such as ALWAYS and TAMPAX, toilet paper such as CHARMIN toilet paper, tissue paper such as PUFFS tissue paper, facial wipes or clothes such as OLAY DAILY FACIAL wipes or clothes, toilet training wipes such as KANDOO pre-moistened wipes, all sold by The Procter & Gamble Company. Still other examples of products include packaging components and substrates and/or containers for laundry detergent and coffee, which may be produced in pellets or pouches and may be manufactured in a converting or web process or even discreet products produced at high speed such as high-speed bottling lines or cosmetics. Still other examples of products include a web substrate containing labels to be placed on bottles and/or containers for laundry detergent (such as Tide, Gain, etc.), fabric enhancers (such as Febreeze, Downy, etc.), hair and beauty care products (such as Head & Shoulders, Old Spice deodorant/antiperspirant, Herbal Essence, Pantene, etc.), and cleaning products (such as Mr. Clean, Cascade, Dawn, Ivory, etc.). Further, it is to be appreciated that although the present disclosure often refers to monitoring or viewing substrates and/or webs, it is to be appreciated that the inspection systems discussed herein can be used to monitor and/or view combinations of webs and individual components as well as parts added as a continuous web of material and parts added as a discontinuous web of material.

FIG. 1 shows a schematic representation of an absorbent article converting process including a converting line or machine 100 configured to manufacture diapers. It is to be appreciated that the systems and methods disclosed herein are applicable to work with various types of converting processes and/or machines. As shown in FIG. 1, the converting line 100 may include one or more motors 102 that drive transport systems, such as a nip roll 104, to move diaper substrates and component materials through the manufacturing process. For example, FIG. 1 shows a base substrate 106 and two auxiliary substrates and/or components 108 of material used to construct portions of the diapers. The substrates may be provided as rolls and fed into the converting line 100. It is to be appreciated that material of the auxiliary substrates may be supplied in various ways. For example, FIG. 1 shows a first auxiliary substrate 110 in the form of a continuous substrate 112, and a second auxiliary substrate 114 in the form of individual components 116. It is to be appreciated that the auxiliary substrates 110 may be transferred to the base substrate through various types of transfer mechanisms. For example, the individual components 116 are shown as being transferred to the base substrate via a transfer mechanism 118 in the form of a servo patch placer mechanism 120, such as disclosed in U.S. Pat. Nos. 6,450,321; 6,705,453; 6,811,019; and 6,814,217. It is also to be appreciated that the various substrates can be used to construct various components of the absorbent articles, such as backsheets, topsheets, and absorbent cores. Exemplary descriptions of absorbent article components are provided below with reference to FIG. 8. Referring back to FIG. 1, as the base substrate 106 advances through the converting line 100, the base substrate 106 is combined with the auxiliary substrates 108 and/or discrete components 116 to create a continuous length of absorbent articles 122. At a downstream portion of the converting process 100, the continuous length of absorbent articles 122 is subjected to a final knife 124 and cut to create separate and discrete absorbent articles 126 in the form of diapers 128. As discussed in more detail below, defective articles 130 may be subject to a rejection system 132 and removed from the process. For example, FIG. 1 shows defective diapers being channeled to a reject bin 136. Diapers 134 that are not deemed to be defective may be subject to further processing steps, such as folding and packaging. For example, FIG. 1 shows non-defective diapers advancing from the final knife 124 to a folding mechanism 138.

It is to be appreciated that various types reject systems 132 may be used to physically remove defective diapers 130. For example, in some embodiments, a pneumatic system may be used to remove defective absorbent articles from the assembly line. More particularly, after application of the final knife and before being folded by a folding mechanism, defective articles 130 are removed from the assembly line by a blast of compressed air discharged from the pneumatic system. In other embodiments, defective articles 130 may be allowed to advance from the final knife 124, partially through a folding mechanism, and into a reject bin. Such a system, described for example in U.S. Patent Publication No. US20080223537A1, may stop or slow the motion of tucker blades on the folding mechanism such that a rejected article will pass through a portion of the folding mechanism without being folded and fall into a reject bin. After the defective articles have passed through the folding mechanism, motion of the tucker blades is resumed, allowing the tucker blades to engage non-defective articles and causing the non-defective articles to be folded and channeled toward a packaging process downstream of the folding mechanism.

As shown in FIG. 1 and as described in more detail below, various sensors 140 and other devices may be arranged adjacent the converting line 100 may communicate with a controller 142. Based on such communications, the controller 142 may monitor and affect various operations on the converting line 100. As discussed in more detail below, the controller may send reject commands 1002 to the reject system based on communications with the sensors 140. In the systems and methods described herein, the controller 142 includes a computer system. The computer system may, for example, include one or more types of programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators.

As the substrates and components travel in the machine direction MD through the converting line, the controller tracks the advancement of the substrates and components. In some embodiments such as shown in FIG. 1, the controller 142 may track the advancement with counts generated by a machine axis 144 that correspond with machine direction positions on substrates and components while advancing though the converting line 100. In some configurations, the machine axis 144 may be configured as an actual motor 146 that provides count signals 1004 to the controller 142. The controller 100 may utilize rotational speed, time, and/or count data from the machine axis 144 that correspond with the machine direction speed and travel of the substrates and components through the converting line 100.

It is to be appreciated that instead of or in addition to utilizing feedback from a physical machine axis as discussed above, the rotational motion of the machine axis 144 may be simulated by software in the controller. For example, in FIG. 1, the controller 100 can utilize counts generated by a virtual machine axis 148 in the controller software. More particularly, the virtual machine axis 148 may be programmed to imitate a motor that generates counts as the motor rotates. As such, it is to be appreciated that the machine axis 144 referred to herein may be either a virtual axis existing in software or a physical axis corresponding with the rotational motion of a motor or other equipment.

Figure 2:
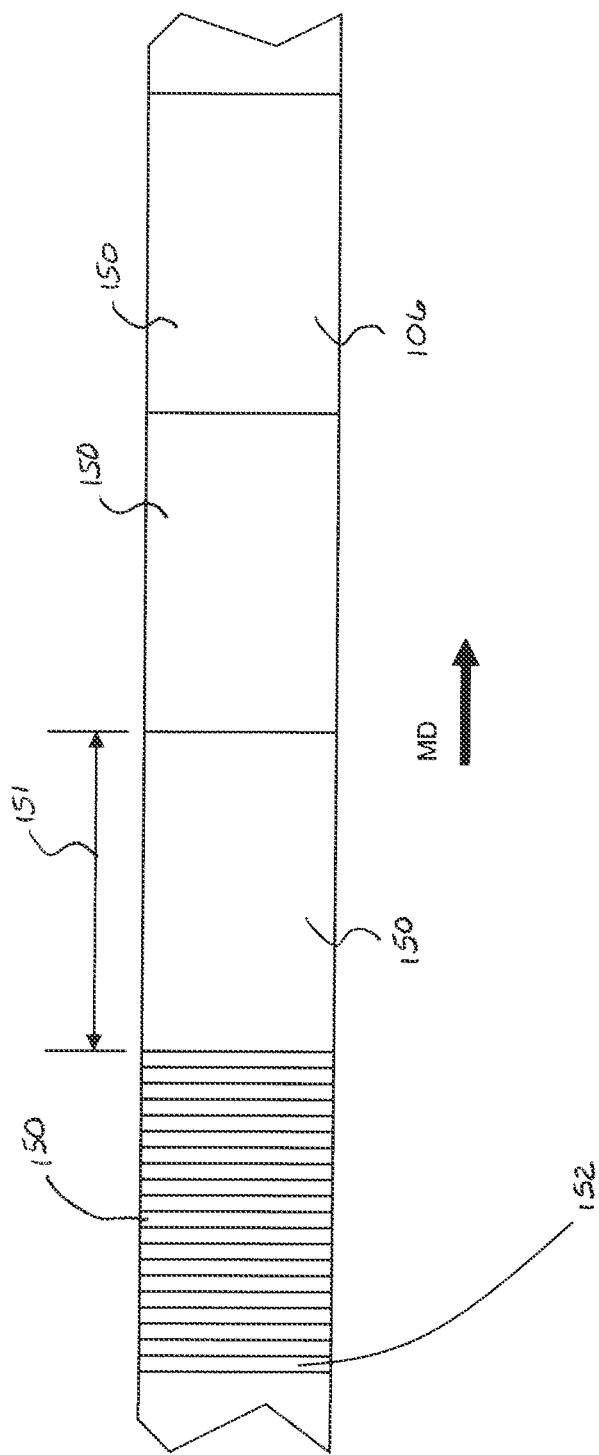
FIG. 2 is a top view of an advancing substrate showing virtual products and virtual segments.
Figure 8:
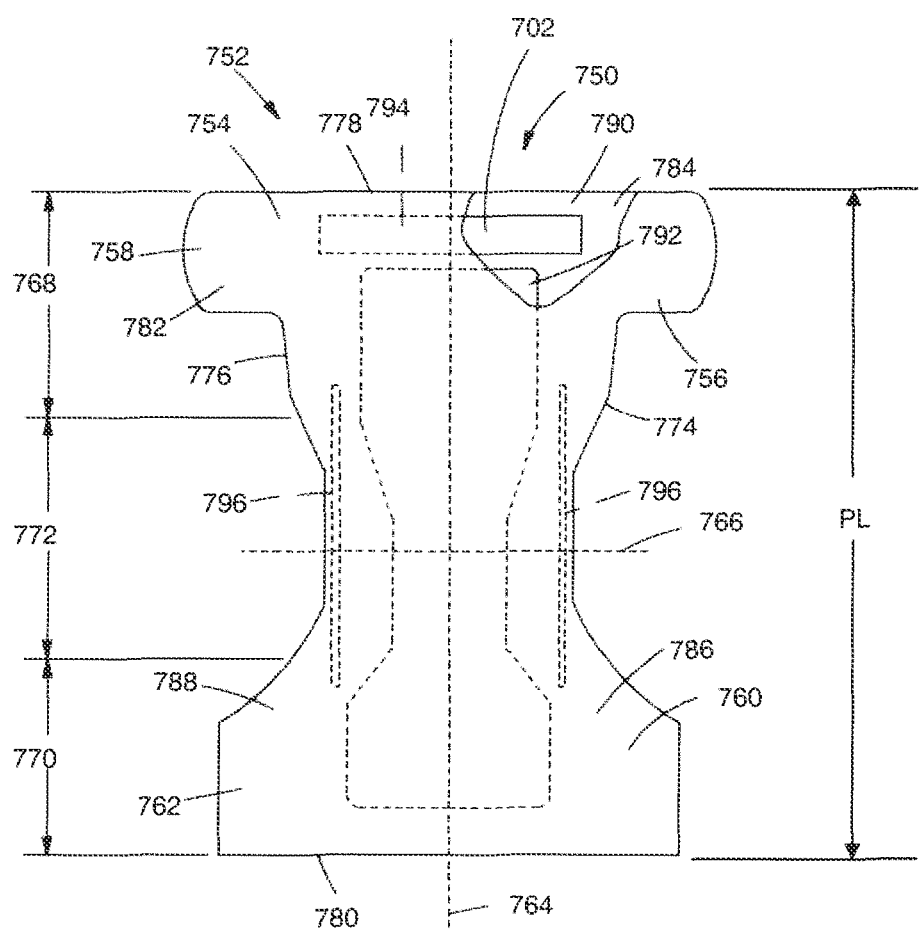
FIG. 8 is a top plan view of a disposable absorbent article that may include one or more substrates and/or components monitored and constructed in accordance with the present disclosure.

As discussed above, the machine axis 144 may be configured to correlate the linear motion of the substrates and components in the machine direction MD through the converting line 100 with counts corresponding with rotation of the machine axis 144. In some embodiments, one complete rotation of the machine axis 144 and associated count data correspond with one pitch length of an absorbent article 126. In some embodiments, the pitch lengths of the absorbent articles are the machine direction longitudinal lengths of the individual absorbent articles being produced. FIG. 8 shows an example of a longitudinal pitch length PL of a diaper. As such, the controller 142 may use counts generated from the machine axis 144 to virtually divide the substrates and components into virtual products 150. As shown in FIG. 2, the virtual products 150 may have machine direction lengths 151 that correspond with the pitch lengths of products being produced. For example, FIG. 2 shows a top side view of the base substrate 106 divided into virtual products 150 along the machine direction MD by the controller 142. Count signals corresponding with rotation of the machine axis that correspond with less than a complete rotation can also be used by the controller divide each virtual product 150 into virtual segments 152, such as shown in FIG. 2. As discussed in more detail below, the substrate speed and estimated clock inaccuracies can be used to determine the length of the each virtual segment in the machine direction MD, and in turn, the number of virtual segments in each virtual product. For example, FIG. 2 shows one virtual product 150 divided into twenty virtual segments 152. As discussed in more detail below, the controller 142 can also utilize signals from the inspection sensor 140 that corresponds with the detection of defects in virtual products and segments to correlate the locations of defects within defective products 130.

As previously mentioned, the systems and methods herein utilize various types of sensors to monitor the substrates and components traveling through the converting line. As shown in FIG. 1, various types of inspection sensors 140 may be used to detect defects in the substrates 106, 108, 110 and/or components 116. In particular, the inspection sensors 140 may detect defects within substrates and/or components themselves, such as for example, damage, holes, tears, dirt, and the like, and may also detect defective assemblies and/or combinations of the substrates and components, such as for example, missing and/or misplaced ears, landing zones, fasteners, and the like. As such, inspection sensors may be configured to detect the presence or absence of substrates and/or components, and may be configured to detect the relative placement of substrates and/or components. As discussed in more detail below, based on the detections of the inspection sensors 140, feedback signals from the inspection sensors in the form of inspection parameters 1000 are communicated to the controller.

It is to be appreciated that various different types of inspection sensors 140 may be used to monitor substrates and various components while advancing through the converting line 100. For example, inspection sensors 140 may be configured as photo-optic sensors that receive either reflected or transmitted light and serve to determine the presence or absence of a specific material; metal-proximity sensors that use electromagnetic to determine the presence or absence of a ferromagnetic material; or capacitive or other proximity sensors using any of a number of varied technologies to determine the presence or absence materials. Inspection sensors 140 may also be configured as vision systems and other sub-processing devices to perform detection and, in some cases, logic to more accurately determine the status of an inspected product. Particular examples of such inspections sensors 140 may include Cognex Insight, DVT Legend or Keyence smart cameras, component vision systems such as National Instruments PXI or PC based vision system such as Cognex VisionPro or any other vision system software which can run on a PC platform.

It should also be appreciated that inspection parameters 1000 may be provided from inspection sensors 140 in various forms. In one embodiment, inspection parameters 1000 may be in the form of "results," such as for example, provided from a sensor state change resulting in a binary input corresponding with the detected presence or absence of a defect, such as for example, the presence or absence of components and/or substrates. For example, inspection parameters 1000 may indicate the presence or absence of an ear, landing zone, and/or printed graphics on a product. In another example, an inspection parameter 1000 may indicate the presence or absence of a tear, hole, splice tape, and/or contaminants in a substrate and/or component. In another embodiment, inspection parameters 1000 may be provided in the form of measurements and/or numerical indications of detected positions of components and/or substrates; numerical indications of the positions of components and/or substrates relative to other components and/or substrate; and/or numerical indications of the positions of components and/or substrates relative to another physical or virtual reference. For example, inspection parameters 1000 may indicate the relative position of one feature, such as a back ear fastener, with respect to a back ear substrate or the measured width of a main chassis compared to the desired width. In other embodiments, inspection parameters 1000 may be in the form of images transferred via a standard protocol such as ftp (File Transfer Protocol), DDE (Dynamic Data Exchange), or OPC (Object Linking and Embedding for Process Control), which are stored in a database or stored in a specified directory on an image server for the purpose of either operator visualization, offline image processing or claim support.

As shown in FIG. 1, the inspection sensors 140 are connected with the controller 142 through a communication network 154, which allows the inspection sensors 140 to communicate inspection parameters 1000 to the controller 142. As discussed in more detail below, devices that communicate on the network each include precision clocks that are synchronized to a master clock within some specified accuracy. As shown in FIG. 1, the inspection sensors 140 and the controller 142 may be connected directly with the communication network 154. As such, each sensor or other field device connected directly with the communication network may include a clock. Inspection sensors 140 that include a clock and that may be connected directly with the communication network 154 may include, for example, vision systems such as National Instruments CVS or any PC-based vision system such as Cognex VisionPro. Such sensors may also include other controllers that may be configured as peers to the controller or may be configured as subordinate to the controller.

In some embodiments, the inspection sensors 140 may be indirectly connected with the communication network 154. For example, the inspections sensors 140 may be connected with the communication network 154 through a remote input and output (I/O) station 156. When utilizing remote I/O stations 156, the inspection sensors 140 may be hardwired to the remote I/O stations, and in turn, the remote I/O stations are connected with the communication network 154. As such, the each remote I/O station 156 may include a precision clock. Example remote I/O stations 156 or other IEEE-1588 based instruments that can be utilized with systems and methods herein include, for example a National Instruments PCI-1588 Interface (IEEE 1588 Precision Time Protocol Synchronization Interface) that synchronizes PXI systems, I/O modules and instrumentation over Ethernet/IP or a Beckhoff Automation EtherCat and XFC technology (eXtreme Fast Control Technology).

As previously mentioned, each device, such as the inspection sensors 140, remote I/O stations 156, and the controller 142, connected with the communication network 154 includes a clock, and each clock is synchronized to a master clock. In one configuration, the controller 142 includes the master clock, and all other clocks of devices connected with the communication network are referenced to the controller master clock. In such a configuration, the remote I/O stations and inspection sensors each include a clock that is synchronized to the controller master clock. Inspection parameters provided by the inspection sensors 140 and communicated to the communication network 154 are time-stamped with the time from the clocks on the corresponding sensors and remote I/O stations. In turn, the inspection parameters and corresponding timestamp data is sent to the controller over the communication network 154. Thus, the controller can be programmed to evaluate the inspection parameter based on the actual time the inspection parameter was provided by the inspection sensor. Therefore, ambiguity as to when detections were actually made by an inspection sensor is relatively small.

As previously mentioned, all clocks that are used to determine and report timestamps may be synchronized together. Clock synchronization allows the reported time from one device on the communication network 154 to be utilized by another device on the communication network. When the clocks are synchronized, ambiguity as to when an inspection parameter was actually provided by the inspection sensor 140 is affected only by the accuracy of the clocks with respect to each other. The clocks of the devices on the communication network may be synchronized in various ways depending on the type of communication network 154 used.

In one embodiment, the communication network 154 is configured as a non-deterministic communication network, such as for example, Ethernet or Ethernet IP (industrial protocol) communication network. When using an Ethernet IP communication network, the clocks of each device may be synchronized using the IEEE1588 precision time protocol, described in IEEE1588 Standard, "Precision Clock Synchronization Protocol for Networked Measurement and Control Systems" and also described in Rockwell Automation publication number 1756-WPO05A-EN-E, published January 2009, and entitled "An Application of IEEE 1588 to Industrial Automation." As mentioned above, timestamps associated with inspection parameters from any inspection sensor may be referenced to the master clock, which allows the relative time as to when the inspection parameters were provided to be accurately calculated. In one configuration, the controller includes the master clock, the controller master clock, and all other clocks of devices connected with the communication network, the sensor clocks, are referenced to the controller master clock. As a result, the time as to when an inspection parameter was provided from an inspection sensor can be can be reported to the controller within the accuracy of an IEEE1588 compliant clock. In some embodiments, reported timestamps may be accurate to within 0.1 milliseconds of the controller master clock. In another configuration, another device, such as an Ethernet switch or router is the local master clock. In this case, both the controller clock and the sensor clock follow the local master clock. The identity of the local master is unimportant since all clocks in the system are synchronized to the local master within the IEEE1588 PTP standard, With reference to the above description and figures, the methods and systems herein utilize a controller 142 and one or more inspection sensors 140 connected with a communication network 154. Each sensor 140, and remote I/O device 156, if used, have clocks that are synchronized with the master controller clock in the controller. The controller 142 tracks the movement of the substrates and components traveling in the machine direction of the converting line 100. More particularly, controller 142 utilizes feedback from the machine axis 144 to virtually divide the substrates and components into virtual products 150 along the machine direction, track the movement of virtual products 150 in the machine direction, and correlate the virtual products 150 to actual individual products 126 produced after the final knife 124 cut. In addition, the controller 142 utilizes feedback from the machine axis 144 to virtually divide the virtual products 150 into virtual segments 152 along the machine direction. The inspection sensors 140 provide inspection parameters 1000 to the controller 142 via the communication network 154. As discussed above, the inspection parameters 1000 can be configured to indicate various types of defects in the substrates and/or components. The sensors 140 provide inspection parameters 1000 to the communication network along with associated timestamp from the sensor clocks. The controller receives the inspection parameters 1000 and associated timestamps from the communication network 154 and correlates the inspection parameters with the corresponding virtual products 150 and/or virtual segment 152 moving along the converting line 100. Once a virtual product 150 is deemed defective, the controller 142 will correlate the defective virtual product 150 with a defective individual product 130, and the controller will send a reject command 1002 the rejection system 132 to reject or cull the defective individual product 130.

To provide additional context to the above discussion, the following provides a specific description of one example implementation of the reject systems and processes herein. FIGS. 3A-7B show an example of an absorbent article converting line 100 as substrates and components travel along the machine direction MD to a final knife cut 124 and a folding and/or packing system 138. In particular, FIGS. 3A, 4A, 5A, 6A, and 7A show schematic side views of the converting line 100, substrates 106, 108 and components 116, and FIGS. 3B, 4B, 5B, 6B, and 7B show a top view of the substrates 106 and components 116 that correspond with FIGS. 3A, 4A, 5A, 6A, and 7A, respectively. For the purposes of the discussion relating to FIGS. 3A-7B, the converting line 100 is described in the context of a diaper converting line. In particular, a base substrate 106 is shown to enter and advance in the machine direction MD through the converting line 100. Material from an auxiliary substrate 108 is cut into individual components 116, transferred and bonded to the base substrate 106 to form features 158 on the base substrate 106, such as for example, front ears on a diaper. FIGS. 3A, 4A, 5A, 6A, and 7A also show an inspection sensor 140, controller 142, machine axis 144, pad reject system 132, and folding system 138 associated with the converting line 100. In accordance with the above description, the machine axis 144 is shown schematically in the form of a virtual axis 148 provides base substrate position and speed signals to the controller 142. In turn, the controller 142 divides the base substrate into virtual products 150 along the machine direction MD. For the purposes of the present description, FIGS. 3A-7B show only three virtual products 150. Also in accordance with the above discussion, the inspection sensor 140 is connected with a remote I/O station 156. In turn, the remote I/O station 156 and controller 142 are connected with a communication network 154, in the form of an Ethernet IP network. It is to be appreciated that the more than inspection sensor 140 may be used and that some or all inspection sensors may be connected directly with the communication network 154 without using a remove I/O station. The remote I/O station includes a clock 1006, referred to herein as a sensor clock 1008 providing a time, Ts, and the controller includes a clock 1006, referred to herein as the master control clock 1010 providing a time, Tc. The sensor clock 1008 is synchronized with the master control clock 1010, such that Ts is set to equal Tc.

Figure 3:
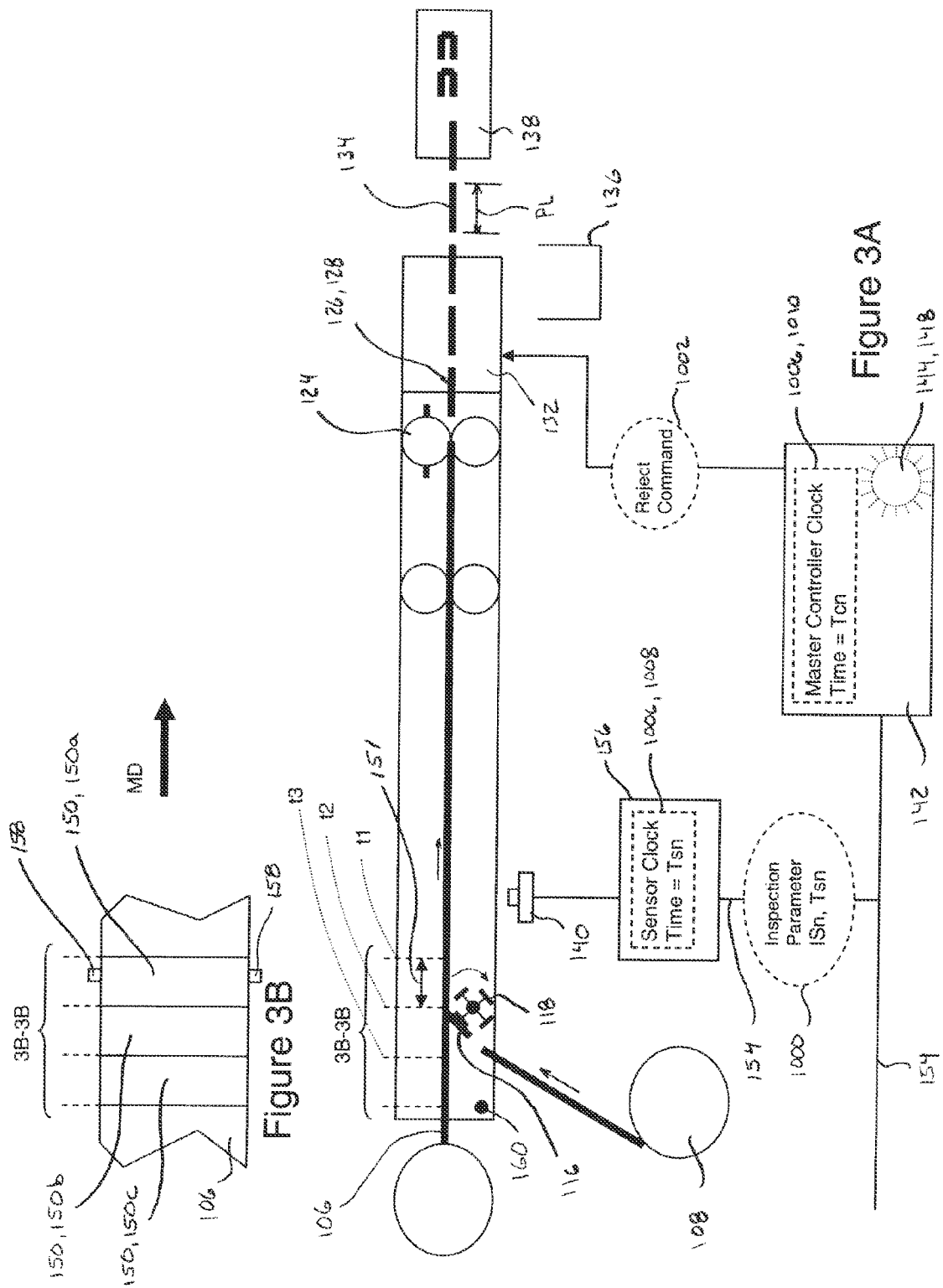
FIG. 3A is a schematic side view of converting line, substrate, and components.
FIG. 3B is a top view of the substrates and components that corresponds with FIG. 3A.
Figure 4:
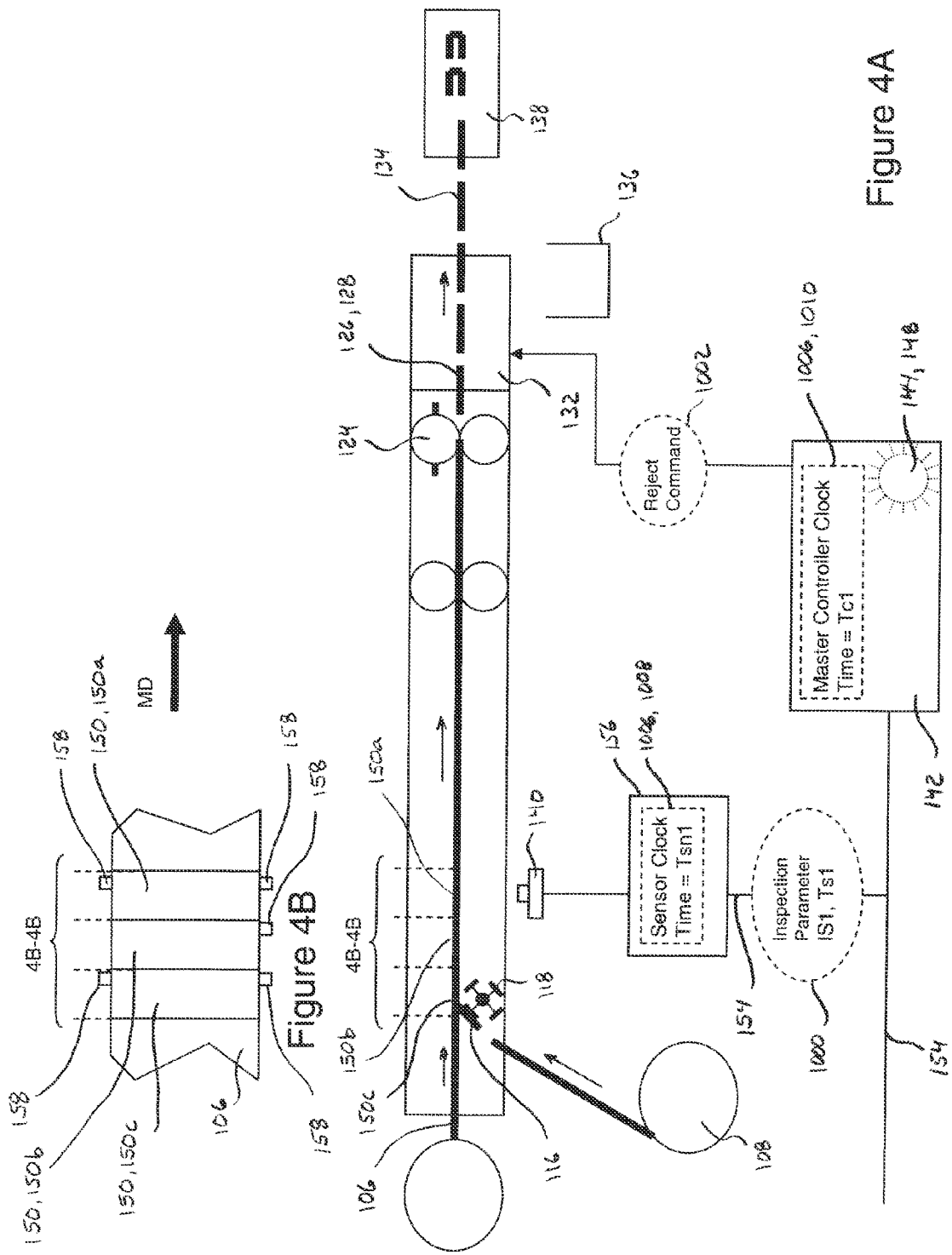
FIG. 4A is a schematic side view of converting line, substrate, and components.
FIG. 4B is a top view of the substrates and components that corresponds with FIG. 4B.
Figure 5:
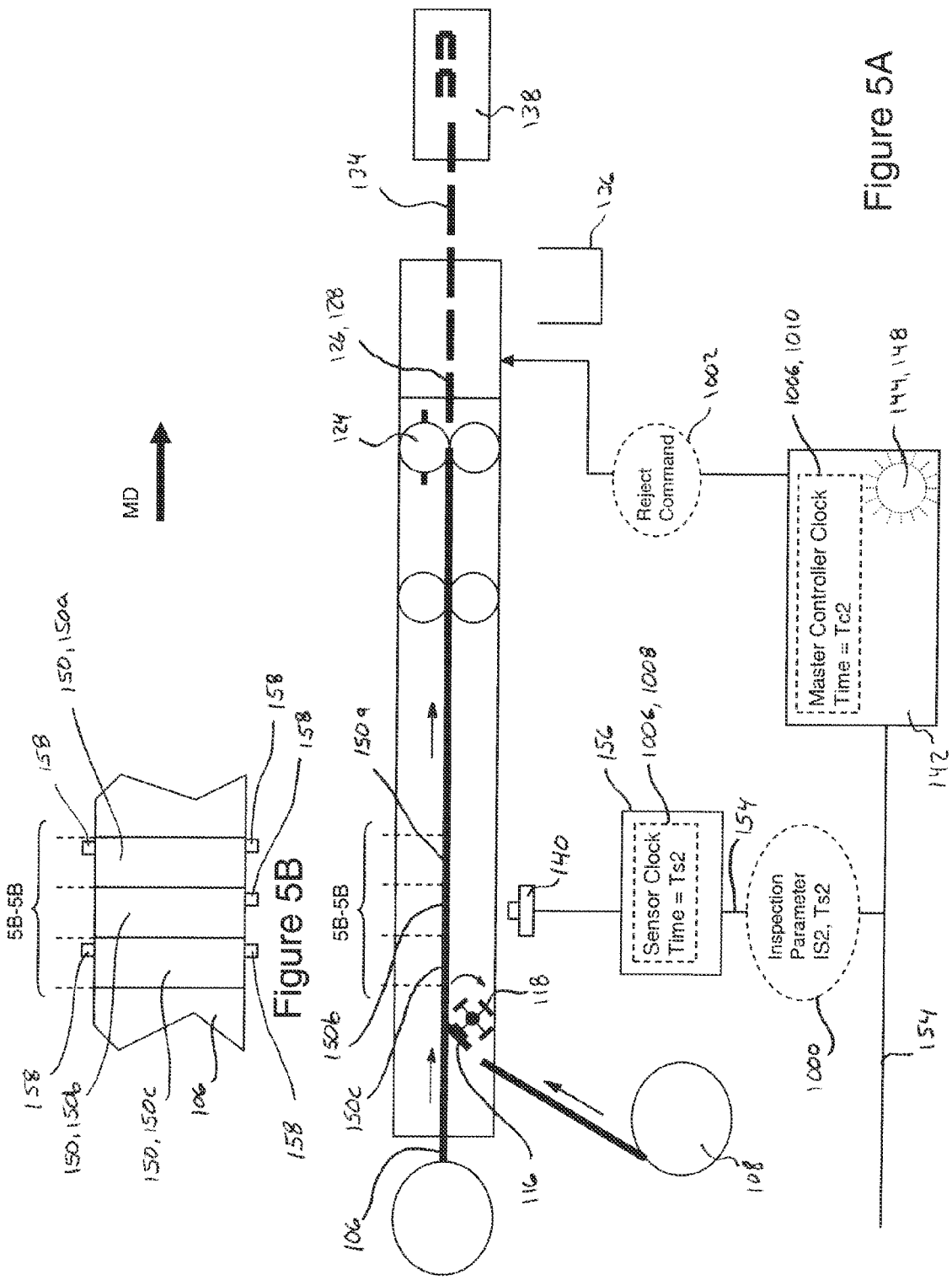
FIG. 5A is a schematic side view of converting line, substrate, and components.
FIG. 5B is a top view of the substrates and components that corresponds with FIG. 5A.
Figure 6:
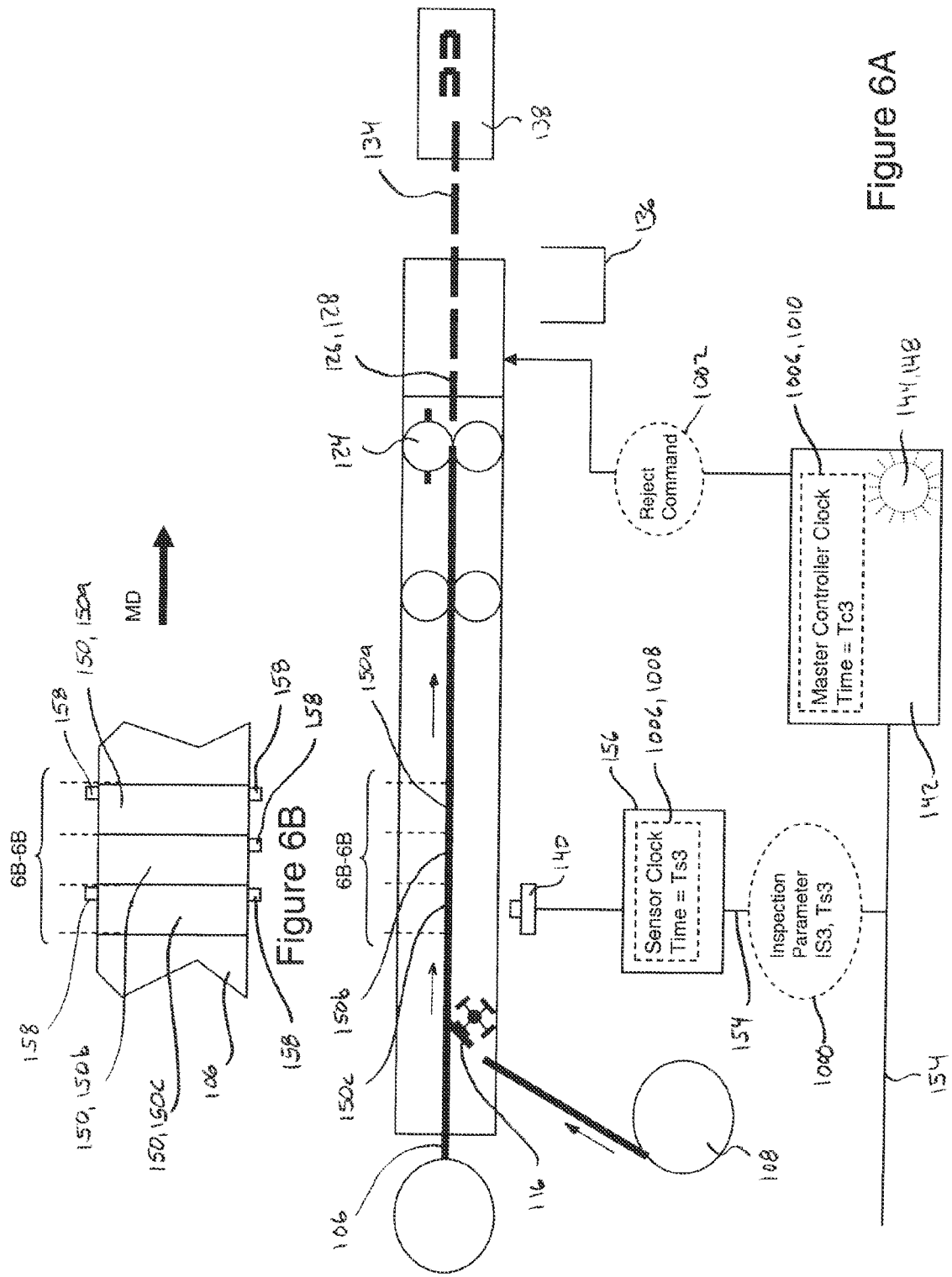
FIG. 6A is a schematic side view of converting line, substrate, and components.
FIG. 6B is a top view of the substrates and components that corresponds with FIG. 6A.
Figure 7:
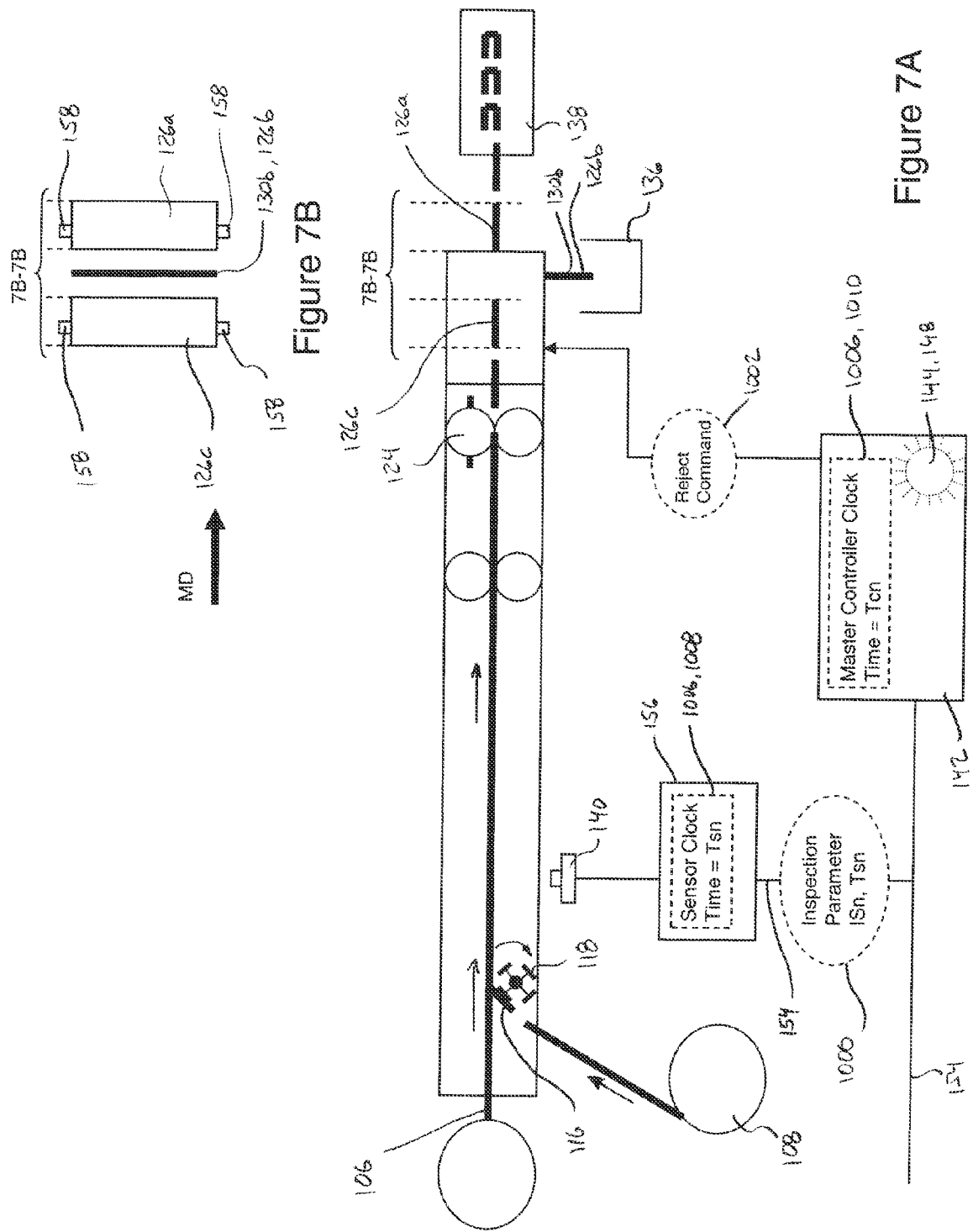
FIG. 7A is a schematic side view of converting line, substrate, and components.
FIG. 7B is a top view of the substrates and components that corresponds with FIG. 7A.

As shown in FIGS. 3A-7A, the lengths 151 of the virtual products 150 in the machine direction correspond with the pitch lengths PL of products 126 being produced. For the purposes of discussion, it is assumed that virtual product pitch length 151 is 600 mm and the base substrate 106 travels in the machine direction at a speed of 300 meters per minute, or 500 products per minute. In the present example, it is assumed that the machine axis 144 rotates such that one complete one rotation corresponds with a one pitch length 151 advancement of the base substrate 106 in the machine direction, and as such, one complete rotation of the machine axis 144 occurs every 120 milliseconds. Upon each revolution of the machine axis 144, a shift register in the controller 142 is incremented by one virtual product 150. For example, FIGS. 3A and 3B show the base substrate 106 advancing in the machine direction MD past a reference point 160 in the converting line 100. At the reference point 160, a first virtual product identified as 150a is present at the reference point at a first time, $t_1$. At a second time, $t_2$, 120 milliseconds after $t_1$, a second virtual product identified as 150b is present at the same reference point, meanwhile the first virtual product 150a has progressed one pitch or 600 mm downstream in the machine direction. Continuing on, at a third time, $t_3$, 120 milliseconds after $t_2$, a third virtual product identified as 150c is present at the same reference point 160, meanwhile the first and second virtual products 150a, 150b have progressed one pitch or 600 mm downstream in the machine direction. The aforementioned increments continue as the base substrate 106 moves through the converting line 100. FIGS. 3A and 3B also show the addition of front ears 158 to the first virtual product 150a.

FIGS. 4A and 4B show the advancement of the base substrate 106 in the machine direction past the inspection sensor 140. As discussed above, the inspection sensor 140 can be configured to perform various detection operations. In one example, the inspection sensor 140 detects the presence or absence of the front ears 158 on the virtual products 150 passing thereby. As such, the inspection sensor 140 provides an inspection parameter 1000 to the communication network via the remote I/O station, wherein the inspection parameter 1000 corresponds with the sensed presence or absence of the front ears 158. In accordance with the above discussion, the inspection parameter includes a corresponding timestamp from the sensor clock 1008. When the position of the inspection sensor 140 along the converting line is known by the controller 142, the controller 142 can correlate the inspection parameters 1000 provided by the inspection sensor 140 with the corresponding virtual products 150 based on the timestamps of the inspection parameters 1000.

FIGS. 4A and 4B show the continued advancement from FIGS. 3A and 3B of the base substrate in the machine direction, and in particular, advancement of the first virtual product past the inspection sensor 140. As shown in FIG. 4B, two front ears 158 are present on the first virtual product 150a. FIG. 4A shows a first inspection parameter, IS1, having a corresponding timestamp, Ts1, being communicated to the communication network 154. IS1 may be configured to provide an indication that both front ears 158 are present on the first virtual product 150a. Simultaneously, the time reported by master controller clock 1010 is Tc1. As discussed below, IS1 may not be immediately received by the controller 142.

Next, FIGS. 5A and 5B show the continued advancement from FIGS. 4A and 4B of the base substrate 106 in the machine direction MD, and in particular, advancement of the second virtual product 150b past the inspection sensor 140. As shown in FIG. 5B, one of the front ears 158 is missing from the second virtual product 150b. FIG. 5A shows a second inspection parameter, IS2, having a corresponding timestamp, Ts2, being communicated to the communication network 154. IS2 provides an indication that one front ear 158 is missing from the second virtual product 150b. Simultaneously, the time reported by master controller clock 1010 is Tc2. Again, IS2 may not be immediately received by the controller 142 from the communication network 154.

Next, FIGS. 6A and 6B show the continued advancement from FIGS. 5A and 5B of the base substrate 106 in the machine direction, and in particular, advancement of the third virtual product 150c past the inspection sensor 140. As shown in FIG. 6B, two front ears 158 are present on the third virtual product 150c. FIG. 6A shows a third inspection parameter, IS3, having a corresponding timestamp, Ts3, being communicated to the communication network 154. IS3 may be configured to provide an indication that both front ears 158 are present on the third virtual product 150c.

Simultaneously, the time reported by master controller clock 1010 is Tc3. Again, IS3 may not be immediately received by the controller 142 from the communication network 154.

As previously mentioned, some amount of time may pass before the controller 142 receives the inspection parameters 1000 from the communication network 154. Such time delays may be the result of the non-deterministic nature of the Ethernet IP network. There may also be additional time before a controller analyzes the inspection parameters based on the controller's program cycle or loop time. However, notwithstanding such time delays, once the controller receives and analyzes inspection parameters, the controller can use the corresponding timestamps of the inspection parameters to correlate the inspection parameters 1000 with particular virtual products 150. For example, the controller may receive and analyze IS2 at some time after IS2 was provided to the communication network 154. However, along with IS2, the controller 142 will receive Ts2, which was provided by the sensor clock 1010. Because the sensor clock 1008 is synchronized with the master controller clock 1010, the controller 142 can correlate IS2 with the second virtual product 150*b*. As discussed above, IS2 may be configured to provide an indication that one front ear 158 is missing from the second virtual product. As such, the controller 142 may deem the second virtual product 150*b* as being defective. In turn, the controller 142 correlates the virtual products 150*a*, 150*b*, 150*c* with individual products 126*a*, 126*b*, 126*c* and may send a signal to the reject system 132 to reject the individual diaper 130*b* that corresponds with the second virtual product 150*b*, such as shown in FIGS. 7A and 7B.

Because the inspection parameters 1000 have timestamps provided from sensor clocks 1008 that are synchronized with the master controller clock 1010, the controller 142 can correlate the inspection parameters 1000 with actual physical locations on the substrates and/or components advancing through the converting line 100 without having to account for various system time delays, such as time delays in the communication network and controller loop times. As such, the correlated location of the inspection parameters on the substrates and/or components may be accurate to within the accuracy of the sensor clock with respect to the master controller clock. For example, where the clock accuracy meets the software implementation of IEE1588, the clocks may be assured to be accurate within 0.1 milliseconds. In such a case, the position of an inspection parameter 1000, such as for IS2 in the example above, may be known to within 0.5 mm in the machine direction MD on the base substrate 106.

Expanding on the above discussion of the example provided in FIGS. 3A-7B, it is to be appreciated that the controller 142 can utilized the machine axis 144 to further divide the virtual products 150 into virtual segments 152, such as described above with reference to FIG. 2. As such, the controller 142 may correlate the inspection parameters 1000 with actual physical locations within the virtual products 150. In accordance with the present disclosure, it is to be further appreciated that the inspection sensors 140 can be configured to provide various types of inspection parameters 1000 that may be utilized by the controller in various ways to execute the rejection of defective products 130. For example, as discussed above, the inspection parameter 1000 may be configured in the form of result that corresponds with the detected presence or absence of a component 116. In another example, the inspection parameter 1000 may be configured in the form of measurement or numerical values that correspond with the positions of substrates and/or components relative to each other or some other physical or virtual reference point. In still another example, the inspection parameter 1000 may be configured in the form of a result that corresponds to a detection of a feature signal from the inspection sensor. Together with the associated timestamp of the received signal, the controller 142 can calculate the position of the feature detection within the virtual product by calculating the virtual segment that corresponds with the received sensor detection at the corresponding sensor timestamp. In that way, the evaluation of a defect can be isolated to a certain position or segment of the product, allowing the controller to correlate the presence of a sensor's input with certain positions within the product, but generating a defect result if the same detection is made in another position within the product. For example, if a sensor is placed to detect the front ear of a diaper and the detection occurs of the leading edge and the trailing edge of the front ear, the detection events, along with the sensor timestamps may be used by the controller to allow the front ear at the front end of the diaper, but to generate a defect result if the front ear is placed in the middle of the diaper. As such, in some configurations, the controller may be configured to simply reject defective products based on defect signals from the inspection sensors. In other examples, the controller may be configured to compare numerical values and/or measurements provided by the inspection sensors to allowable limits in order to determine if products are defective. In yet other examples, the controller may analyze images provided by the inspection sensors to determine if products are defective.

As previously mentioned, the systems and methods herein may be used to monitor various types of substrates and components during the manufacture of various different products. For the purposes of a specific illustration, FIG. 8 shows one example of a disposable absorbent article 750, such as described in U.S. Patent Publication No. US2008/0132865 A1, in the form of a diaper 752 that may be constructed from substrates and components monitored according to the systems and methods disclosed herein. In particular, FIG. 8 is a plan view of one embodiment of a diaper 752 including a chassis 754 shown in a flat, unfolded condition, with the portion of the diaper 752 that faces a wearer oriented towards the viewer. A portion of the chassis structure is cut-away in FIG. 8 to more clearly show the construction of and various features that may be included in embodiments of the diaper.

As shown in FIG. 8, the diaper 752 includes a chassis 754 having a first ear 756, a second ear 758, a third ear 760, and a fourth ear 762. To provide a frame of reference for the present discussion, the chassis is shown with a longitudinal axis 764 and a lateral axis 766. The chassis 754 is shown as having a first waist region 768, a second waist region 770, and a crotch region 772 disposed intermediate the first and second waist regions. The periphery of the diaper is defined by a pair of longitudinally extending side edges 774, 776; a first outer edge 778 extending laterally adjacent the first waist region 768; and a second outer edge 780 extending laterally adjacent the second waist region 770. As discussed above, the pitch length, PL, of the absorbent article 750 may be defined by the distance between the first outer edge 778 and the second outer edge 780. As shown in FIG. 8, the chassis 754 includes an inner, body-facing surface 782, and an outer, garment-facing surface 784. A portion of the chassis structure is cut-away in FIG. 8 to more clearly show the construction of and various features that may be included in the diaper. As shown in FIG. 8, the chassis 754 of the diaper 752 may include an outer covering layer 786 including a topsheet 788 and a backsheet 790. An absorbent core 792 may be disposed between a portion of the topsheet 788 and the backsheet 790. As discussed in more detail below, any one or more of the regions may be stretchable and may include an elastomeric material or laminate as described herein. As such, the diaper 752 may be configured to adapt to a specific wearer's anatomy upon application and to maintain coordination with the wearer's anatomy during wear.

As previously mentioned, the chassis 754 of the diaper 752 may include the backsheet 790, shown for example, in FIG. 8. In some embodiments, the backsheet is configured to prevent exudates absorbed and contained within the chassis from soiling articles that may contact the diaper, such as bedsheets and undergarments. Some embodiments of the backsheet may be fluid permeable, while other embodiments may be impervious to liquids (e.g., urine) and comprises a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, and microporous films. Suitable breathable composite materials are described in greater detail in PCT Application No. WO 95/16746, published on Jun. 22, 1995 in the name of E. I. DuPont and U.S. Pat. No. 5,865,823, both of which are hereby incorporated by reference herein. Other breathable backsheets including nonwoven webs and apertured formed films are described in U.S. Pat. Nos. 5,571,096 and 6,573,423, which are all hereby incorporated by reference herein.

The backsheet 790, or any portion thereof, may be stretchable in one or more directions. In one embodiment, the backsheet may comprise a structural elastic-like film ("SELF") web. Embodiments of SELF webs are more completely described in U.S. Pat. Nos. 5,518,801; 5,723,087; 5,691,035; 5,916,663; and 6,027,483, which are all hereby incorporated by reference herein. In some embodiments, the backsheet may comprise elastomeric films, foams, strands, nonwovens, or combinations of these or other suitable materials with nonwovens or synthetic films. Additional embodiments include backsheets that comprise a stretch nonwoven material; an elastomeric film in combination with an extensible nonwoven; an elastomeric nonwoven in combination with an extensible film; and/or combinations thereof. Details on such backsheet embodiments are more completely described in U.S. Publication Nos. US2007/0287348A1; US2007/0287982A1; and US2007/0287983A1, which are all hereby incorporated by reference herein. The backsheet 790 may be joined with the topsheet 788, the absorbent core 792, and/or other elements of the diaper 752 in various ways. For example, the backsheet may be connected with a uniform continuous layer of adhesive, a patterned layer of adhesive, or an array of separate lines, spirals, or spots of adhesive. One embodiment utilizes an open pattern network of filaments of adhesive as disclosed in U.S. Pat. No. 4,573,986, which is hereby incorporated by reference herein. Other embodiments utilize several lines of adhesive filaments which are swirled into a spiral pattern, as is illustrated by the apparatus and methods shown in U.S. Pat. Nos. 3,911,173; 4,785,996; and 4,842,666, which are all hereby incorporated by reference herein. In some embodiments, the backsheet is connected with heat bonds, pressure bonds, ultrasonic bonds, dynamic mechanical bonds, or any other suitable attachment means or a combination thereof.

The topsheet 788 may be constructed to be compliant, soft feeling, and non-irritating to the wearer's skin. Further, all or at least a portion of the topsheet 788 may be liquid pervious, permitting liquid to readily penetrate therethrough. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929,135; 4,324,246; 4,342,314; 4,463,045; and 5,006,394, all of which are hereby incorporated by reference herein. Other topsheets may be made in accordance with U.S. Pat. Nos. 4,609,518 and 4,629,643, both of which are hereby incorporated by reference herein.

In some embodiments, the topsheet 788 is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988,344 and 4,988,345, all of which are hereby incorporated by reference herein. A more detailed discussion of some methods for incorporating surfactant in the topsheet can be found in U.S. Statutory Invention Registration No. H1670, which was published on Jul. 1, 1997, in the names of Aziz et al., all of which are hereby incorporated by reference herein. In some embodiments, the topsheet 788 may include an apertured web or film that is hydrophobic. This may be accomplished eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos. 5,342,338; 5,941,864; 6,010,491; and 6,414,215, all of which are hereby incorporated by referenced herein.

The absorbent core 792 may include absorbent material that is generally compressible, conformable, non-irritating to the wearer's skin, and capable of absorbing and retaining liquids such as urine and other body exudates. The absorbent core 792 can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures are described in U.S. Pat. Nos. 4,610,678; 4,673,402; 4,834,735; 4,888,231; 5,137,537; 5,147,345; 5,342,338; 5,260,345; 5,387,207; and 5,650,222, all of which are hereby incorporated by reference herein.

The absorbent core 792 may also have a multiple layered construction. A more detailed discussion of various types of multi-layered absorbent cores can be found in U.S. Pat. Nos. 5,669,894; 6,441,266; and 5,562,646; European Patent No. EP0565606B1; U.S. Patent Publication No. 2004/0162536A1; 2004/0167486A1; and PCT Publication No. WO 2006/015141, which are all hereby incorporated by reference herein. In some embodiments, the absorbent article includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to collect forces tending to move the article on the wearer. The absorbent article may also include an elastic waist feature 702 shown in FIG. 8 in the form of a waist band 794 and may provide improved fit and waste containment. The elastic waist feature 702 may be configured to elastically expand and contract to dynamically fit the wearer's waist. The elastic waist feature 702 can be incorporated into the diaper in accordance with the methods discussed herein and may extend at least longitudinally outwardly from the absorbent core 792 and generally form at least a portion of the first and/or second outer edges 778, 780 of the diaper 752. In addition, the elastic waist feature may extend laterally to include the ears. While the elastic waist feature 702 or any constituent elements thereof may comprise one or more separate elements affixed to the diaper, the elastic waist feature may be constructed as an extension of other elements of the diaper, such as the backsheet 790, the topsheet 788, or both the backsheet and the topsheet. In addition, the elastic waist feature 702 may be disposed on the outer, garment-facing surface 784 of the chassis 754; the inner, body-facing surface 782; or between the inner and outer facing surfaces. The elastic waist feature 702 may be constructed in a number of different configurations including those described in U.S. Patent Publication Nos. 2007/0142806; 2007/0142798; and 2007/0287983, all of which are hereby incorporated by reference herein.

Although the first and second ears 756, 158 as well as the third and fourth ears 760, 762 shown in FIG. 8 are illustrated as being integrally formed with the chassis 754, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306, which are all hereby incorporated by reference herein. The ears may also include various geometries and arrangements of stretch zones or elements, such as discussed in U.S. Pat. Publication Nos. US2005/0215972A1 and US2005/0215973A1, which are all hereby incorporated by reference herein.

As shown in FIG. 8, the diaper 752 may include leg cuffs 796 that may provide improved containment of liquids and other body exudates. The leg cuffs 796 may be disposed in various ways on the diaper 752. For example, the leg cuffs 796 may be disposed on the outer, garment-facing surface 784 of the chassis 754; the inner, body-facing surface 782; or between the inner and outer facing surfaces. Leg cuffs 796 may also be referred to as leg bands, side flaps, barrier cuffs, or elastic cuffs. U.S. Pat. No. 3,860,003, which is hereby incorporated by reference herein, describes a disposable diaper that provides a contractible leg opening having a side flap and one or more elastic members to provide an elasticized leg cuff (a gasketing cuff). U.S. Pat. Nos. 4,808,178 and 4,909,803, which are both hereby incorporated by reference herein, describe disposable diapers having "stand-up" elasticized flaps (barrier cuffs). U.S. Pat. Nos. 4,695,278 and 4,795,454, which are both hereby incorporated by reference herein, describe disposable diapers having dual cuffs, including gasketing cuffs and barrier cuffs. In some embodiments, it may be desirable to treat all or a portion of the leg cuffs with a lotion, as described above. In addition to leg cuffs, diaper can also include an elastic gasketing cuff with one or more elastic strands positioned outboard of the barrier cuff. The leg cuffs may be treated with a hydrophobic surface coating, such as described in U.S. Pat. Publication No. 20060189956A1, which is hereby incorporated by reference herein.

The diaper 752 may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274, which are all hereby incorporated by reference herein. Additional examples of fasteners and/or fastening elements are discussed in U.S. Pat. Nos. 6,251,097 and 6,432,098; and U.S. Patent Publication Nos. 2007/0078427 and 2007/0093769, which are all hereby incorporated by reference herein. Other fastening systems are described in more detail in U.S. Pat. Nos. 5,595,567; 5,624,427; 5,735,840; and 5,928,212, which are all hereby incorporated by reference herein. The fastening system may also provide a means for holding the article in a disposal configuration as disclosed in U.S. Pat. No. 4,963,140, which is hereby incorporated by reference herein.

It is to be appreciated that the methods and systems disclosed herein may be utilized to monitor the quality of substrates and components as well as respective placements during the manufacture of absorbent articles, such as for example, topsheets, backsheets, absorbent cores, ears, waist features, and graphics printed thereon. It is also to be appreciated that the reject systems and methods described herein may also be utilized in combination with other types of control systems and methods, such as described in U.S. patent application Ser. No. 12/476,479, entitled "SYSTEMS AND METHODS FOR CONTROLLING PHASING OF ADVANCING SUBSTRATES IN ABSORBENT ARTICLE CONVERTING LINES," filed on Jun. 2, 2009, and U.S. patent application Ser. No. 12/476,348, entitled "SYSTEMS AND METHODS FOR CONTROLLING REGISTRA- TION OF ADVANCING SUBSTRATES IN ABSORBENT ARTICLE CONVERTING LINES," filed on Jun. 2, 2009. Further, the time synchronization features of the methods and systems described herein may be utilized in other types of control systems and methods such as for example: data storage and correlation methods with repeat application devices and multiple application stations such as described in U.S. Pat. No. 6,829,516; raw material database integration such as described in U.S. Pat. No. 7,162,319; web guide control methods and systems such as described in U.S. Pat. No. 6,801,828; and data mining and trending methods and systems such as described in U.S. Pat. No. 6,845,278.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for rejecting defective absorbent products from a web converting manufacturing process, the method comprising the steps of:
   providing a communication network;
   connecting a sensor with the communication network, the sensor including a sensor clock;
   connecting a controller with the communication network, the controller including a controller clock;
   synchronizing the sensor clock with the controller clock such that the reported time of the controller clock and the sensor clock can be correlated;
   advancing a substrate in a machine direction through a converting process;
   virtually segmenting the substrate into a plurality of virtual segments;
   sequentially adding component parts to the substrate;
   inspecting at least one of the substrate and component parts with the sensor;
   communicating inspection parameters from the sensor to the communication network;
   assigning a timestamp to each inspection parameter, each timestamp based on the sensor clock;
   receiving the inspection parameters and corresponding timestamps from the communication network into the controller;
   correlating each inspection parameter with one virtual segment based on the timestamp of the inspection parameter;
   identifying defects in virtual segments based on the inspection parameters;
   cutting the substrate with component parts added thereto into discrete absorbent articles; and
   rejecting absorbent articles that correspond with virtual segments with identified defects.

2. The method of claim 1, wherein the component parts include parts added as a continuous web of material and parts added as a discontinuous web of material.

3. The method of claim 1, wherein the communication network is non-deterministic.

4. The method of claim 1, wherein one inspection parameter comprises a result.

5. The method of claim 1, wherein one inspection parameter corresponds to a detected defect to the substrate.

6. The method of claim 1, wherein one inspection parameter corresponds to a detected missing component on the substrate.

7. The method of claim 1, wherein one inspection parameter corresponds to measured placement of a component on the substrate.

8. The method of claim 1, wherein the absorbent articles are diapers.

9. The method of claim 8, wherein the component parts are ears.

10. A method for rejecting defective absorbent products from a web converting manufacturing process, the method comprising the steps of:
    providing a communication network;
    connecting a sensor to a remote I/O station and connecting the remote I/O station to the network, the remote I/O station including a sensor clock;
    connecting a controller with the communication network, the controller including a controller clock;
    synchronizing the sensor clock with the controller clock such that the reported time of the controller clock and the sensor clock can be correlated;
    advancing a substrate in a machine direction through a converting process;
    virtually segmenting the substrate into a plurality of virtual segments;
    sequentially adding component parts to the substrate;
    inspecting at least one of the substrate and component parts with the sensor;
    communicating inspection parameters from the sensor to the communication network;
    assigning a timestamp to each inspection parameter, each timestamp based on the sensor clock;
    receiving the inspection parameters and corresponding timestamps from the communication network into the controller;
    correlating each inspection parameter with one virtual segment based on the timestamp of the inspection parameter;
    identifying defects in virtual segments based on the inspection parameters;
    cutting the substrate with component parts added thereto into discrete absorbent articles; and
    rejecting absorbent articles that correspond with virtual segments with identified defects.

11. The method of claim 10, wherein the component parts include parts added as a continuous web of material and parts added as a discontinuous web of material.

12. The method of claim 10, wherein the communication network is non-deterministic.

13. The method of claim 10, wherein one inspection parameter comprises a result.

14. The method of claim 10, wherein one inspection parameter corresponds to a detected defect to the substrate.

15. The method of claim 10, wherein one inspection parameter corresponds to a detected missing component on the substrate.

16. The method of claim 10, wherein one inspection parameter corresponds to measured placement of a component on the substrate.

17. The method of claim 10, wherein the absorbent articles are diapers.

18. The method of claim 17, wherein the component parts are ears.

* * * * *